United States Patent [19]

Minami

[11] Patent Number: 5,723,652
[45] Date of Patent: Mar. 3, 1998

[54] OPTICALLY ACTIVE MONOPHOSPHINO CARBOXYLIC ACID DERIVATIVE

[75] Inventor: Tohru Minami, Munakata, Japan

[73] Assignee: Nissan Chemical Industries, Ltd., Tokyo, Japan

[21] Appl. No.: 672,036

[22] Filed: Jun. 26, 1996

[30] Foreign Application Priority Data

Jun. 28, 1995 [JP] Japan ................................. 7-162584

[51] Int. Cl.$^6$ .......................... C07C 69/67; C07C 59/11
[52] U.S. Cl. ..................... 560/179; 562/579; 560/254; 560/265
[58] Field of Search .................. 560/179; 562/579; 568/17

[56] References Cited

U.S. PATENT DOCUMENTS 3,686,351  8/1972  Mason .

FOREIGN PATENT DOCUMENTS 0 184 872   6/1986   European Pat. Off. .
0 327 743   8/1989   European Pat. Off. .
5 306291   11/1993   Japan .

OTHER PUBLICATIONS

Tetrahedron Letters, vol. 31, No. 27, pp. 3905–3908, 1990, Yoshiharu Okada, et al., "The First Synthesis of Chiral Phosphinocarboxylic Acid Ligands, Trans–2–(Diphenylphosphino)Cycloalkanecarboxylic Acids. The Phosphine–Palladium Complexes Catalyzed Asymmetric Allylic Alkylation".

Tetrahedron: Asymmetry, vol. 2, No. 7, pp. 667–682, 1991, Yoshiharu Okada, et al., "Synthesis of a Novel Type of Chiral Phosphinocarboxylic Acids. The Phosphine–Palladium Complexes Catalyzed Asymmetric Allylic Alkylation".

Tetrahedron: Asymmetry, vol. 6, No. 10, pp. 2469–2474, 1995, Toru Minami, et al., "Development of Chiral Phosphine Ligands Bearing a Carboxyl Group and Their Application to Catalytic Asymmetric Reaction".

J. Am. Chem. Soc., vol. 116, 4089–4090, 1994, Barry M. Trost, et al., "Asymmetric Induction in Allylic Alkylations of 3-(Acyloxy)Cycloalkenes".

J. Chem. Soc., Chem. Commun., pp. 1845–1846, 1995, Guido Knuehl, et al., "New Chiral β–Phosphinocarboxylic Acids and Their Application in Palladium–Catalysed Asymmetric Allylic Alkylations".

Chem. Rev., vol. 96, pp. 395–422, 1996, Barry M. Trost, et al., "Asymmetric Transition Metal–Catalyzed Allylic Alkylations".

Tetrahedron, vol. 33, pp. 2615–2649, 1977, Barry M. Trost, "Organopalladium Intermediates in Organic Sysnthesis".

Tetrahedron, vol. 42, No. 16, pp. 4361–4401, 1986, Jiro Tsuji, "New General Synthetic Methods Involving π-Allylpalladium Complexes as Intermediates and Neutral Reaction Conditions".

Chemistry Letters, pp. 613–616, 1986, Toru Minami, et al., "Synthesis and Resolution of a New Type of Chiral Bisphosphine Ligand, Trans–Bis–1,2–(Diphenylphosphino)Cyclobutane, and Asymmetric Hydrogenation Using Its Rhodium Complex".

Phosphorus, Sulfur Silicon Relat. Elem., vol. 42, No. 3–4, pp. 211–222, 1989, J. A. Van Doorn, et al., "Synthesis of Some Functionalized Phosphinocarboxylic Acids".

J. Organomet. Chem., vol. 468, No. 1–2, pp. 99–106, 1994, Kerstin Heesche-Wagner, et al., "Approaches to Water–Soluble Phosphines. II. Free Radical Addition Reactions of Phenylphosphines".

*Primary Examiner*—Gary Geist
*Assistant Examiner*—Jean F. Vollano
*Attorney, Agent, or Firm*—Oblon, Spivak, McClelland, Maier & Neustadt, P.C.

[57] ABSTRACT

The invention is to provide an asymmetric reaction catalyst useful for the production of medical or agricultural chemicals or intermediates thereof. The catalyst comprises an optically active monophosphino carboxylic acid derivative represented by the formula (I):

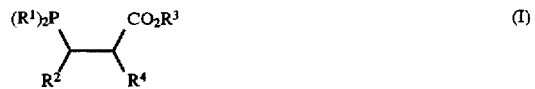

where $R^1$ represents a $C_{1-6}$ alkyl group or phenyl group which may be optionally substituted with a $C_{1-4}$ alkyl group or $C_{1-4}$ alkoxy group, $R^2$ represents a $C_{1-4}$ alkyl group, $R^3$ and $R^4$ each represents independently a hydrogen atom, $C_{1-4}$ alkyl group or phenyl group which may be optionally substituted with a $C_{1-4}$ alkyl or $C_{1-4}$ alkoxy group and a transition metal compound.

5 Claims, No Drawings

OPTICALLY ACTIVE MONOPHOSPHINO CARBOXYLIC ACID DERIVATIVE

(TECHNICAL FIELD)

The present invention concerns an asymmetric reaction catalyst and a ligand therefor which is useful for the production of medical or agricultural chemicals or intermediates thereof.

(PRIOR ART)

It is important that biologically active agents are optically active substances since biobodies on which they act have asymmetric structures and, upon production of biologically active agents such as medical or agricultural chemicals, it has been strongly demanded socially to produce and provide only the optically active substances in view of reduction in side-effects and environmental protection. Development of the process for synthesizing optically active compounds is an important subject of study for satisfying such a demand, and has been studied energetically world-wide both in official and civil organizations. Among all, development of the process for producing optically active compounds using asymmetric reaction catalysts is extremely useful for the chemical synthesis industry since this enables to produce optically active compounds in a great amount from a small amount of asymmetric source.

Heretofore, a number of asymmetric reaction catalysts have been developed ("Homogeneous Catalysis with Metal Phosphine Complex", ed. by L. H. Pignolet, Plenum Press, New York, 1983) and, among them, several practical methods have been reported for asymmetric oxidizing catalysts and asymmetric reduction catalysts ("Asymmetric Synthesis", Vol. 5, ed. by J. D. Morrison, Academic Press, Orlando (1985)). However, with a view point of industrial application, there are still left many problems to be solved such as economical advantages or reaction condition of catalysts and, while several studies at the laboratory level have been seen, for example, in an asymmetric allylating reaction catalyst exemplified specifically as an example of the present invention (B. M. Trost, Tetrahedron, 33, 2615 (1977); R. F Heck, "Palladium Reagents in Organic Synthesis", Academic Press, London, 117 (1985); J. Tsuji, Tetrahedron, 42, 4361 (1986) (hereinafter referred to as literature a), Japanese Patent Application Hei 5-306291 (hereinafter referred to as literature b)), development of a catalyst which can be utilized industrially has been demanded.

(SUMMARY OF THE INVENTION)

The present inventor has earnestly investigated an economical and highly selective asymmetric allylation catalyst which can be utilized industrially and, as a result, has found that a monophosphino carboxylic acid derivative represented by the formula (I) can be an asymmetric ligand capable of satisfying the purpose, and has accomplished the present invention.

Namely, an optically active monophosphino carboxylic acid derivative represented by the formula (I):

(I)

where $R^1$ represents a $C_{1-6}$ alkyl group or a phenyl group optionally substituted with a $C_{1-4}$ alkyl group or $C_{1-4}$ alkoxy group, $R^2$ represents a $C_{1-4}$ alkyl group, and $R^3$ and $R^4$ each represents independently a hydrogen atom, $C_{1-4}$ alkyl group or phenyl group which may be optionally substituted with a $C_{1-4}$ alkyl group or $C_{1-4}$ alkoxy group, is a type of asymmetric ligand that has not been known at all. Since the asymmetric ligand represented by the formula (I) can be easily produced from inexpensive starting materials as shown in examples, it is a highly economical asymmetric ligand, and a transition metal complex thereof can be a reaction catalyst upon production of an optically active compound. Particularly, the palladium complex is a catalyst suitable for the asymmetric allylating reaction. A prominent feature of the transition metal catalyst comprising the ligand represented by the formula (I) is that the application field thereof is largely extended since it can be utilized as an effective homogeneous catalyst both in water or a solvent mixture of water and an organic solvent due to its water solubility. Application fields of conventional asymmetric reaction catalysts having organic ligands have been restricted due to its water insolubility. Further, the ligand represented by the formula (I) can form complexes with various transition metal compounds and can be various asymmetric reaction catalysts depending on the kinds of central metals of the complexes. For example, the present inventor has already disclosed that a rhodium complex of this type can be an extremely useful asymmetric reduction catalyst (Minami et al., Chem. Lett., 1988, 613). Further, in common with (ortho-diphenylphosphino) benzoic acid—nickel complex (R. F. MASON, U.S. Pat. No. 3,686,351) found by Shell Co., it can be expected that the nickel complex of the present ligand is an asymmetric polymerization catalyst for propylene.

The monophosphino carboxylic acid derivative of the present invention represented by the formula (I) is to be explained in detail below.

Substituents for the compound (I) according to the present invention are as shown below.

$R^1$ represents a $C_{1-6}$ alkyl group, or phenyl group which can be optionally substituted with a $C_{1-4}$ alkyl group or $C_{1-4}$ alkoxy group.

The $C_{1-6}$ alkyl group may be linear, branched or cyclic and there can be mentioned, for example, methyl, ethyl, n-propyl, i-propyl, c-propyl, n-butyl, s-butyl, t-butyl c-butyl, n-pentyl, i-pentyl, 2-methylbutyl, neopentyl, 1-ethylpropyl, c-pentyl, n-hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl and c-hexyl.

The phenyl group may optionally be substituted with a $C_{1-4}$ alkyl group or $C_{1-4}$ alkoxy group, in which the number of substituents can be from 1 to 5, and the alkyl group and the alkoxy group may be present either alone or together. Further, the phenyl group may have no substituent.

The $C_{1-4}$ alkyl group may be linear, branched or cyclic and there can be mentioned, for example, methyl, ethyl, n-propyl, i-propyl, c-propyl, n-butyl, s-butyl, t-butyl and c-butyl.

The $C_{1-4}$ alkoxy group may be linear, branched or cyclic and there can be mentioned, for example, methoxy, ethoxy, n-propoxy, i-propoxy, c-propoxy, n-butoxy, i-butoxy, s-butoxy, t-butoxy and c-butoxy.

$R^1$ is preferably a phenyl group which may be optionally substituted with a $C_{1-4}$ alkyl group or $C_{1-4}$ alkoxy group is preferred.

$R^2$ represents a $C_{1-4}$ alkyl group. As the $C_{1-4}$ alkyl group, there can be mentioned those described above.

$R^3$ and $R^4$ each represents independently a hydrogen atom, $C_{1-4}$ alkyl group or phenyl group which may be optionally substituted with a $C_{1-4}$ alkyl group or $C_{1-4}$ alkoxy group.

As the $C_{1-4}$ alkyl group or the phenyl group which may be optionally substituted with a $C_{1-4}$ alkyl group or $C_{1-4}$ alkoxy group, there can be mentioned those described above.

As the compounds according to the present invention there can be mentioned, preferably, an optically active monophosphino carboxylic acid derivative represented by the formula (I) in which $R^1$ represents a phenyl group which may be optionally substituted with a $C_{1-4}$ alkyl group or $C_{1-4}$ alkoxy group, and $R^3$ and $R^4$ each represents independently a hydrogen atom or $C_{1-4}$ alkyl group.

A production process for the compound according to the present invention is to be explained below. The monophosphino carboxylic acid derivative of the formula (I) according to the present invention can be produced, for example, by the process shown by the following reaction schemes:

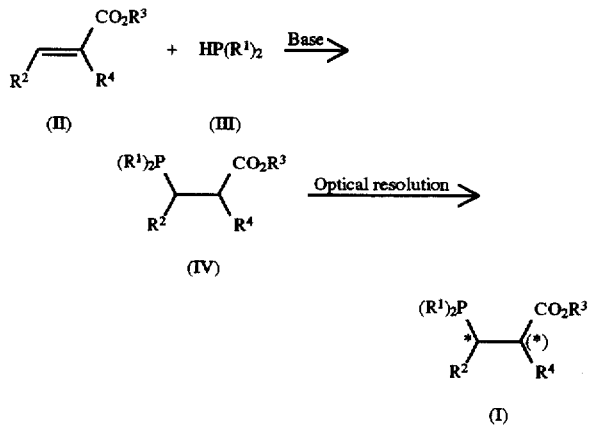

That is, a substituted acrylic acid derivative represented by the formula (II) is reacted with a phosphine compound (III) in the presence of a base to obtain a (±)-monophosphino carboxylic acid derivative (IV), which is subjected to optical resolution and if necessary, to separation of diastereomers, to produce an optically active monophosphino carboxylic acid derivative represented by the formula (I).

The mark "*" in the formula (I) indicates that the absolute configuration on the indicated asymmetric carbon is either R or S, while the mark "(*)" indicates that the absolute configuration of $R^4$ on the asymmetric carbon to which the substituents except for the hydrogen atom is bonded is R or S, or a mixture thereof.

The molar ratio between the starting materials in the reaction can be set freely but it is usually sufficient to use 1 to 5 moles, preferably 1.2 to 2 moles of the phosphine compound represented by the formula (III) per mole of the substituted acrylic acid derivative of the formula (II).

As the base, various kinds of metal bases can be used, for example, n-butyl lithium, t-butyl lithium, phenyl lithium, lithium diisopropylamide, lithium hydride, sodium hydride, calcium hydride and sodium amide.

There is no particular restriction for the reaction solvent so long as it is a solvent not interfering with the reaction and there can be used, for example, ethers such as tetrahydrofuran, 1,4-dioxane, diethyl ether and 1,2-dimethoxyethane, benzene type solvents such as benzene, toluene and xylene, alkanes such as hexane and pentane, amide type solvents such as N,N-dimethylformamide and N-methylpyrrolidone, hexamethyl phosphoric triamide (HMPA), dimethyl sulfoxide (DMSO) or a mixed solvent thereof.

The reaction is usually conducted within a range from $-100°$ C. to room temperature and often conducted, preferably, from $-80°$ C. to $-10°$ C.

As a method of obtaining the optically active monophosphino carboxylic acid derivative represented by the formula (I) according to the present invention from a (±)-monophosphino carboxylic acid derivative represented by the formula (IV), optical resolution methods employed usually can be used. For example, it can be produced by a chromatographic separation method using an optically active column, a preferential crystallization method, or an asymmetric hydrolysis method of a carboxylic acid ester (IV) using an enzyme such as lipase (reaction kinetic resolution method; An optically active phosphino carboxylic acid ester and an optically active phosphino carboxylic acid as an epimer thereof can be obtained).

In a case of (±)-carboxylic acid (IV) in which $R^3$ is a hydrogen atom, a diastereomer salt resolution method using an optically active amine can be used and satisfactory results are often obtained by this method. Accordingly, also in a case of obtaining an optically active monophosphino carboxylic acid ester (I) ($R^3 \neq H$), a synthetic route of subjecting a corresponding (±)-monophosphino carboxylic acid ester (IV) once to hydrolyzing reaction to lead it into a (±)-monophosphino carboxylic acid, and then subjecting it to diastereomer salt resolution using an optically active amine to obtain an optically active monophosphino carboxylic acid, which is subjected to an esterifying reaction employed conventionally, may be adopted.

As the optically active amine used, there can be mentioned naturally occurring alkaloids such as quinine, quinidine, cinchonine, brucine and ephedrine, basic amino acids such as lysine and arginine or optically active synthetic amines such as α-methylbenzylamine, α-ethylbenzylamine, 1-(p-tolyl)ethylamine and 1-phenyl-2-(p-tolyl)ethylamine.

Another production process comprising condensing a racemic carboxylic acid (IV) with an optically active alcohol or optically active amine to obtain an ester or amide as a diastereomeric mixture, which is subjected to diastereomer separation using recrystallization or various kinds of chromatography, and then successively to hydrolysis to obtain an optically active monophosphino carboxylic acid (I) can be also adopted. For the optically active alcohol or amine used and the reaction conditions and operation procedures after using them in the method, those used in the usual optical resolution method may be adopted with no troubles.

The optically active monophosphino carboxylic acid derivative (I) thus obtained is a novel compound and extremely useful as a ligand of asymmetric reaction catalyst. The ligand can form complexes with various transition metal compounds.

As examples of the transition metal compounds, there can be mentioned hydrochlorides, sulfates, nitrates, acetates, phosphine or carbonyl complexes of titanium, vanadium, chromium, manganese, molybdenum, tin, copper, zinc, iron, cobalt, nickel, ruthenium, rhodium, palladium, osmium, iridium or platinum. As specific examples, there can be mentioned palladium hydrochloride, palladium sulfate, palladium nitrate and palladium acetate. They can be asymmetric reaction catalysts, for example, for asymmetric alkylating reaction, asymmetric allylating reaction, asymmetric reducing reaction, asymmetric oxidizing reaction and asymmetric addition reaction by changing the kind of transition metal compounds or reaction conditions. It is not particularly necessary to isolate them but a complex may be formed in a reaction system by adding a ligand and a transition metal compound to the system. In this case, the amount of the transition metal compound added is from 0.01 to 10 molar equivalents, preferably, from 0.1 to 2 molar equivalents on the basis of the ligand. The amount of the catalyst used is from 0.01 mol % to 20 mol %, preferably, 0.1 mol % to 5 mol %. There are no particular restriction for the reaction temperature and the reaction solvent and they may depend on the kind of the reaction to be conducted. Further, other ligands such as imidazole derivative, pyridine derivative or phosphine derivative may be optionally present together.

A complex of a palladium salt selected from the transition metal compounds described above, with the compound (I) according to the present invention is an asymmetric reaction catalyst particularly effective for the asymmetric allylating reaction. The allylating reaction mentioned herein can include a wide variety type of allylating reactions as disclosed, for example, in the literature (a) described previously. The reaction pattern can be represented, for example, as the following reaction scheme.

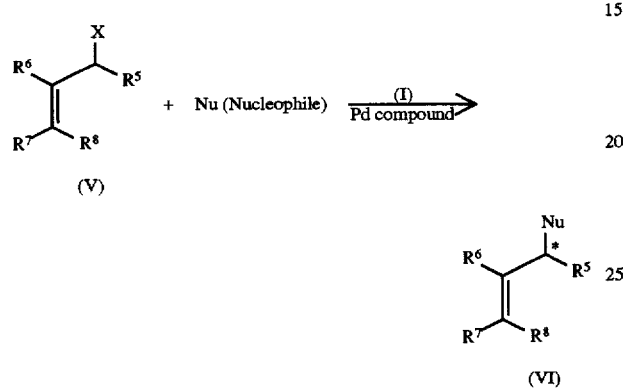

In the reaction formula, $R^5$, $R^6$, $R^7$ and $R^8$ each represents independently a hydrogen atom, alkyl group or aryl group, or $R^5$ and $R^6$, $R^6$ and $R^7$ or $R^5$ and $R^8$ may join to form a $C_{4-7}$ cycloalkyl or cycloalkenyl ring, wherein, the alkyl group may be substituted at any position with an alkoxy group or acyl group; X represents an acyloxy group, alkoxycarbonyloxy group, dialkylaminocarbonyloxy group, dialkylamino group, nitro group, sulfonic group, dialkylphosphonyloxy group or chloro atom; Nu represents a carbon nucleophilic agent usually used in organic synthesis chemistry such as β-ketoester derivative, malonic acid derivative, cyano acetic acid derivative, β-ketophosphonic acid derivative, phosphonyl acetic acid derivative, cyanomethyl phosphonic acid derivative, alkyl or aryl thiomethyl phosphonic acid derivative and various kinds of ester derivatives thereof, or represents a nitrogen nucleophilic agent such as various kinds of primary or secondary amine, amide, phosphoric acid amide derivative or sulfone amide derivative.

The asymmetric allylating reaction represented by the reaction scheme described above can result in excellent asymmetric induction using the asymmetric catalyst formed from the optically active phosphine carboxylic acid ligand (I) and the palladium salt instead of a 0-valent palladium complex used in the allylating reaction described, for example, in the literature (a). It has been shown that the asymmetry inducing capacity of the present asymmetric catalyst is larger in comparison with the capacity of the catalyst described in the literature (b).

While the present reaction can be conducted under a neutral condition, the reaction may proceed or be completed rapidly when it is conducted with addition of various kinds of organic bases or inorganic metal bases such as trialkylamines, alkyl metal hydrides, metal hydrogen carbonate and metal carbonates. For other reaction conditions, those as described in the previous section relating to various kinds of asymmetric reactions, as well as those similar to the reaction condition disclosed, for example, in the literature (a) may be adopted with no troubles.

The optically active allylated derivative obtained according to the present invention is useful as biologically active compounds such as medicines and agricultural chemicals and as intermediates for the production thereof.

(EXAMPLE)

The present invention is to be described more in details with reference to examples (reference examples, synthetic examples and asymmetric catalytic reaction examples) but the present invention is not restricted to such examples at all.

Each term of "IR", "NMR" and "MS" means "infrared absorption spectrum", "nuclear magnetic resonance spectrum" and "mass analysis spectrum", respectively.

Reference Example 1

(±)-t-butyl-3-diphenylphosphino butanoate

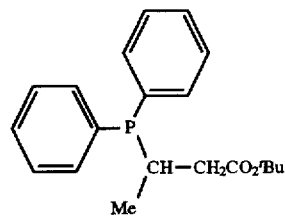

Under argon atmosphere, a solution of n-butyl lithium in hexane (7.32 ml, 12 mmol) was added to a solution of diphenylphosphine (2.23 g, 12 mmol) in tetrahydrofuran (14 ml) at −78° C. and stirred at that temperature for 30 min. Hexamethylphosphoric triamide (2.09 ml, 12 mmol) was added thereto and the temperature was once elevated to 0° C. to dissolve the solidified hexamethyl phosphoric triamide and then rapidly lowered to −78° C. Successively, t-butyl chrotonate (1.42 g, 10 mmol) was added and stirred at that temperature for 10 min, and then an aqueous saturated solution of ammonium chloride was added followed by extraction with ether. After washing the organic layer with water and drying over anhydrous sodium sulfate, the solvent was distilled off under a reduced pressure and the residue was purified by silica gel column chromatography (ether/hexane=1/3) to obtain the above captioned compound.

Amount obtained: 2.6 g

Yield: 79%

$^1$H-NMR(CDCl$_3$) δ1.11(dd, J$_{d(H-H)}$=7.0 Hz, J$_{d(P-H)}$=15.0 Hz, 3H, CH$_3$), 1.48(s, 9H, t-Bu), 1.70–2.80(m, 3H, CH$_2$ and CH), 7.33–7.52(m, 10H, Ar-H).

Reference Example 2

(±)-3-diphenylphospino butanoic acid

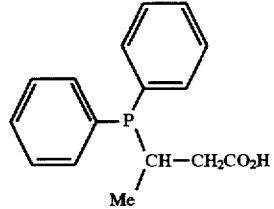

Under argon atmosphere, p-toluene sulfonic acid (7.61 g, 40 mmol) was added to a solution of (±)-t-butyl-3-diphenylphosphino butanoate (2.60 g, 7.9 mmol) in benzene (20 ml) and the mixture was refluxed under heating for three hours. The reaction solution was concentrated under a reduced pressure and the residue was dissolved with chloroform, washed with water and dried over anhydrous sodium sulfate. Successively, the solvent was distilled off under a reduced pressure and the residue was purified by silica gel column chromatography to obtain the above captioned compound.

Amount obtained: 2.07 g

Yield: 76%

IR(neat) 1710 cm$^{-1}$ $^1$H-NMR(CDCl$_3$) δ1.11(dd, J$_{d(H-H)}$=7.0 Hz, J$_{d(P-H)}$=15.0 Hz, 3H, CH$_3$), 2.19(ddd, J$_{d(H-H)}$=16.0, 11.1Hz, J$_{d(P-H)}$=5.2Hz, 1H, CH$_2$), 2.50(ddd, J$_{d(H-H)}$=15.8, 3.4Hz, J$_{d(P-H)}$=8.2Hz, 1H, CH$_2$), 2.86(dddq, J$_{q(P-H)}$=7.0Hz, J$_{d(H-H)}$=11.1, 3.4Hz, J$_{d(P-H)}$=17.9Hz, 1H, CH$_2$), 7.33–7.52(m, 10H, Ar-H).

$^{31}$P-NMR(CDCl$_3$)δ–0.67(s) (from H$_3$PO$_4$)

EIMS m/z 272 (M$^+$)

Example 1

(+)-3-diphenylphosphino butanoic acid

Under argon atmosphere, (±)-3-diphenylphosphino butanoic acid (2.0 g, 7.4 mmol) was dissolved in acetone (5 ml), to which (+)-phenethylamine (0.55 ml, 4.4 mmol) was added and stirred under heating for 30 min. The temperature was lowered to −78° C., and elevated up to 0° C. simultaneously with deposition of crystals and kept for three hours to completely crystallize the ammonium salt. After being filtered under a nitrogen atmosphere and washed with a mixed solvent of ethyl acetate/hexane (1/9), the crystals were dried and the optical rotation thereof was measured. Further, the ammonium salt was recrystallizzed repeatedly with ethyl acetate/hexane until the change of the optical rotation values was no more recognized. The salt was dissolved into chloroform and washed with 2N-hydrochloric acid to form the carboxylic acid. After distilling off the solvent under a reduced pressure, the residue was purified by silica gel chromatography to obtain the above captioned compound.

Amount obtained: 620 mg

Optical rotation: [α]$_D$=+22.0°.

Example 2

(−)-3-diphenylphosphino butanoic acid

The above-captioned compound was obtained by the same procedures as in Example 1 except that (−)-phenethylamine was used instead of (+)-phenethylamine in Example 1.

Optical rotation [α]$_D$=−21.9°

Asymmetric Catalytic Reaction Example 1

(Asymmetric Allylating Reaction)

Under argon atmosphere, a solution of (−)-3-diphenylphosphino butanoic acid (17 mg, 0.06 mmol) in tetrahydrofuran (4 ml) prepared in Example 2 was added to palladium acetate (7 mg, 0.03 mmol). After confirming the formation of a palladium complex by means of turbidity of the solution, cyclohexenyl acetate (0.21 g, 1.5 mmol) was added. Ethyl diethylphosphono acetate carbo anions prepared from sodium hydride (0.08 g, 2.0 mmol) and ethyl diethylphosphono acetate (0.50 g, 2.2 mmol) were added thereto. After stirring at 60° C. for 4 hours, 2N-hydrochloric acid was added to the reaction mixture, which was extracted with ethyl acetate and dried over anhydrous sodium sulfate. After distilling off the solvent under a reduced pressure, optically active ethyl 2-cyclohexenyl diethyl phosphono acetate was obtained by purification with silica gel thin layer chromatography.

Amount obtained: 0.46 g

Yield: 100%

Optical Yield: 77% ee

IR(neat) 1730, 1650, 1250 cm$^{-1}$ $^1$H-NMR(CDCl$_3$)δ 1.29(t, J=7.0Hz, 3H, CH$_3$), 1.34(t, J=7.0Hz, 6H, CH$_3$), 1.4–2.2(m, 6H, CH$_2$), 2.4–3.2(m, 2H, CH), 4.11(q, J=7.0Hz, 2H, CO$_2$CH$_2$), 4.22(q, J=7.0Hz, 4H, POCH$_2$), 5.2–6.2(m, 2H, CH=CH).

The optical yield in the asymmetric allylating reaction was determined after conversion of the product into a diastereomeric amide, as shown below.

Determination of Optical Yield

Under argon atmosphere, sodium hydride (62.9 mg, 1.6 mmol) was added to a tetrahydrofuran solution (4 ml) of ethyl 2-cyclohexenyldiethyl phosphono acetate (0.40 g, 1.31 mmol) obtained by the asymmetric allylating reaction described above. After stirring at a room temperature for 30 min, paraformaldehyde (0.12 g, 4.0 mmol) was added and stirred at the room temperature for further 3 hours. After the reaction was completed, the 2N-hydrochloric acid was added and after extracting the reaction solution with ethyl acetate, the organic phase was dried over anhydrous sodium sulfate. After distilling off the solvent under a reduced pressure an optically active ethyl 2-(2-cyclohexenyl) acrylate was obtained by purification with silica gel thin layer chromatography (benzene/hexane=1/1).

Amount obtained: 0.22 g

Yield: 91.7%

Optical rotation: [α]$_D$=59.0 (c=1.66, CH$_2$Cl$_2$)

Further, an aqueous solution (4 ml) of sodium hydroxide (0.11 g, 2.75 mmol) was added to a solution of ethyl 2-(2-cyclohexenyl) acrylate (0.10 g, 0.55 mmol) in ethanol (8 ml) and the mixture was refluxed under heating for 2 hours. After the hydrolysis was completed, 2N-hydrochloric acid was added to the reaction mixture, which was extracted with chloroform and then dried over anhydrous sodium sulfate. After distilling off the solvent under a reduced pressure, to the residue a solution of 2-chloro-1-methyl pyridinium pyridinium iodide (0.21 g, 0.83 mmol) in dichloromethane (3 ml) was added. A solution of triethylamine (0.23 ml, 1.65 mmol) and (+)-phenethylamine (0.10 ml, 0.83 mmol) in dichloromethane (2 ml) was added thereto and stirred at a room temperature for 3 hours. After the reaction was completed, 2N-hydrochloric acid was added to the reaction mixture, which was extracted with chloroform and then dried over anhydrous sodium sulfate. The solvent was distilled off under a reduced pressure and the resultant compound was analyzed by high performance liquid chromatography, to determine the optical yield in the asymmetric allylating reaction.

I claim:

1. A composition comprising an enantiomeric excess of at least one isomer of a compound of formula (I):

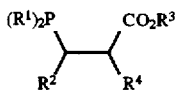

wherein

R$^1$ represents a C$_{1-6}$ alkyl group or a phenyl group which may be optionally substituted with a C$_{1-4}$ alkyl group or C$_{1-4}$ alkoxy group;

R$^2$ represents a C$_{1-4}$ alkyl group; and

R$^3$ and R$^4$ each represents, independently, a hydrogen atom, C$_{1-4}$ alkyl group or a phenyl group which may be optionally substituted with a C$_{1-4}$ alkyl or C$_{1-4}$ alkoxy group.

2. The composition of claim 1, wherein R$^1$ represents a phenyl group which may be optionally substituted with a C$_{1-4}$ alkyl group or C$_{1-4}$ alkoxy group; and R$^3$ and R$^4$ each represents, independently, a hydrogen atom or a C$_{1-4}$ alkyl group.

3. The composition of claim 1, wherein R$^4$ is a hydrogen atom.

4. The composition of claim 1, wherein R$^2$ is a phenyl group.

5. The composition of claim 1, wherein R$^2$ is a phenyl group and R$^4$ is a hydrogen atom.

* * * * *